US00PP25330P3

(12) United States Plant Patent
Skelton

(10) Patent No.: US PP25,330 P3
(45) Date of Patent: Mar. 10, 2015

(54) ***ACTINIDIA DELICIOSA* PLANT NAMED 'MERLE'**

(50) Latin Name: *Actinidia deliciosa*
Varietal Denomination: Merle

(71) Applicant: Donald Alfred Skelton, Huntly (NZ)

(72) Inventor: Donald Alfred Skelton, Huntly (NZ)

( * ) Notice: Subject to any disclaimer, the term of this patent is extended or adjusted under 35 U.S.C. 154(b) by 42 days.

(21) Appl. No.: 13/986,591

(22) Filed: May 15, 2013

(65) Prior Publication Data

US 2014/0345008 P1 Nov. 20, 2014

(51) Int. Cl.
*A01H 5/00* (2006.01)

(52) U.S. Cl.
USPC ..... Plt./156

(58) Field of Classification Search
USPC ..... Plt./156
See application file for complete search history.

*Primary Examiner* — Kent L Bell

(57) ABSTRACT

A new and distinct *Actinidia deliciosa* cultivar named 'MERLE' is disclosed, characterized by having exceptionally long fruit, and a very early seasonal harvest time in New Zealand. Additionally, the new variety produces fruit with a distinctive weakly blunt, protruding stylar end shape. The new variety is suitable for commercial production of kiwi fruit.

3 Drawing Sheets

Figure 1:
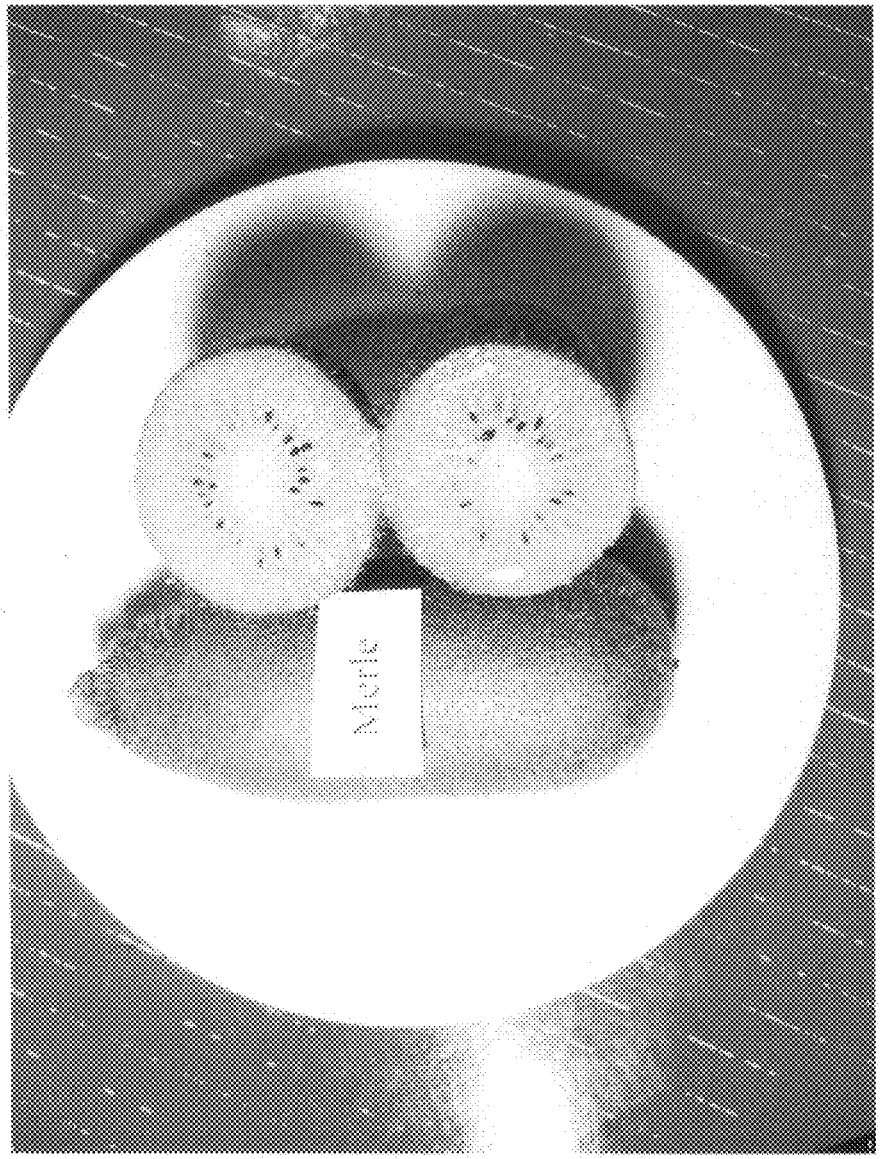

Latin name of the genus and species: *Actinidia deliciosa.*
Variety denomination: 'MERLE'.

BACKGROUND OF THE INVENTION

The new cultivar is a product of a planned breeding program under the direction of the inventor, Donald Alfred Skelton, a citizen of New Zealand. The seed parent is the unpatented, known commercial variety referred to as *Actinidia deliciosa* 'Gracie'. The pollen parent is the unpatented, proprietary seedling variety referred to as *Actinidia deliciosa* 'Blue'.

Fruit of the new variety was first evaluated in 2001 with favorable results. After the first evaluation, semi-hardwood cuttings were made of 'MERLE' and were grafted onto seedling rootstocks of *A. deliciosa*. Evaluation, asexual propagation and grafting all first took place at a research nursery in North Waikato, New Zealand. Subsequent evaluations of the variety have shown the characteristics to be true to type.

SUMMARY OF THE INVENTION

The cultivar 'MERLE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MERLE' These characteristics in combination distinguish 'MERLE' as a new and distinct *Actinidia deliciosa* cultivar:

1. Exceptionally long, obovate shaped fruit form
2. Early flower set.
3. Heavy fruit weight, similar to the known variety 'Hayward'.

4. Weakly blunt protruding stylar fruit end.
5. Yellow-Green fruit coloration.
6. Very early season fruit harvest.

COMPARISON TO PARENT

Plants of the new cultivar 'MERLE' are similar to plants of the seed parent, *Actinidia deliciosa* 'Gracie' in most horticultural characteristics, however, plants of the new cultivar 'MERLE' produce larger fruit. Additionally, 'MERLE' produces a different shaped fruit than 'Gracie'.

Plants of the new cultivar 'MERLE' are similar to plants of the male parent, *Actinidia deliciosa* 'Blue' in some horticultural characteristics. However, as the sex expression of 'Blue' is male, plants of 'Blue' produce male flowers, whereas the sex expression of 'MERLE' is female, and plants produce female flowers that in turn develop into large fruit.

COMMERCIAL COMPARISON

The new variety is best compared to the commercial variety, 'Hort16A', U.S. Plant Pat. No. 11,066. 'MERLE' is similar to 'Hort16A' in many horticultural characteristics, however, 'MERLE' produces mature fruit approximately 2 weeks earlier in the season than 'Hort16A'. Additionally, fruit of the new variety 'MERLE' are distinctively longer and more missile shaped than fruits of 'Hort16A.' Fruit differences can also be noted in the weight. Fruit produced by plants of 'MERLE' are heavier than fruits produced by 'Hort16A'.

The new variety can be compared to the commercial variety, 'Hayward', unpatented. 'MERLE' is similar to 'Hayward' in many horticultural characteristics, however, 'MERLE' produces mature fruit several weeks earlier in the season than 'Hayward'. Additionally, fruit of the new variety 'MERLE' are distinctively long, missile shaped whereas fruits of 'Hayward' is typically broad and obovate. Additionally, 'Merle' has an interior fruit coloration with a stronger yellow tone.

BRIEF DESCRIPTION OF THE PHOTOGRAPH

The accompanying photograph in FIG. 1 illustrates in full color examples of typical fruit harvested from 'MERLE'.

Figure 2:
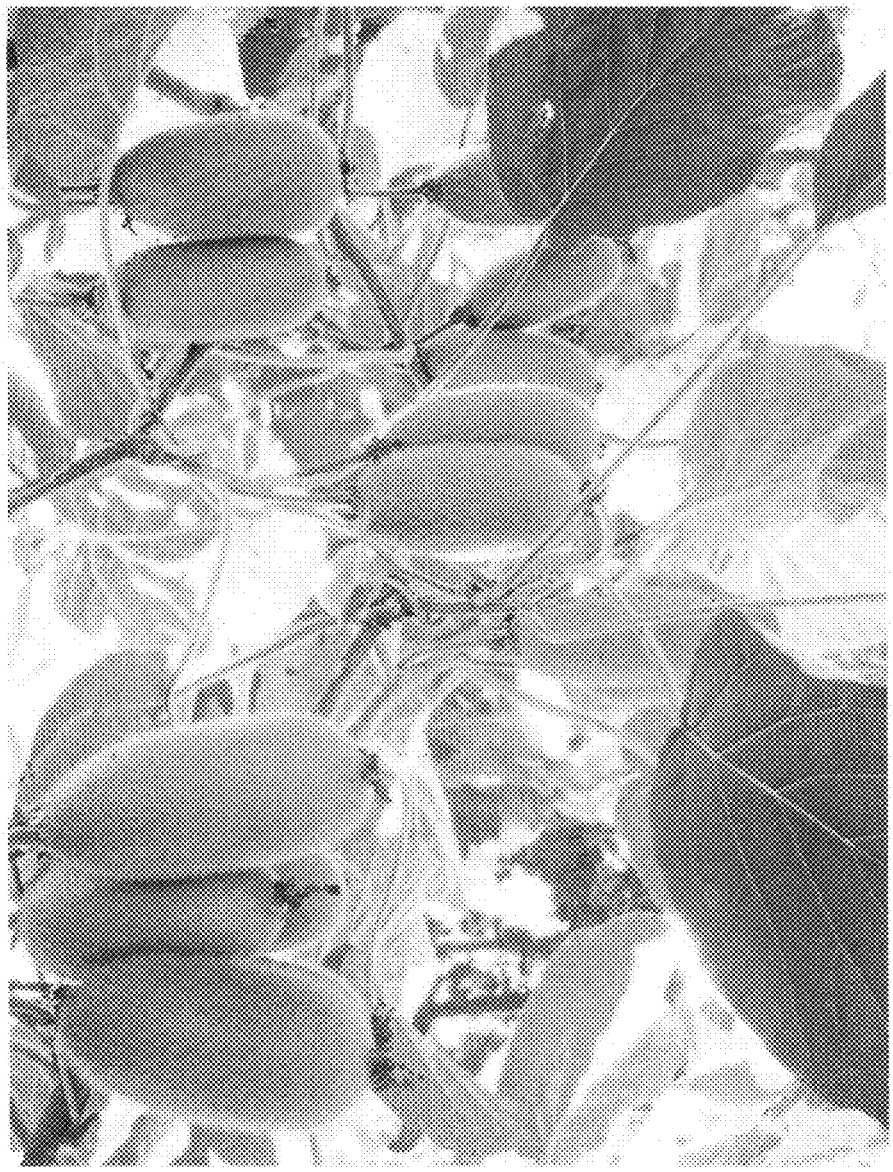

FIG. 2 illustrates in full color typical foliage, hanging fruit and stems on plants of 'MERLE'.

Figure 3:
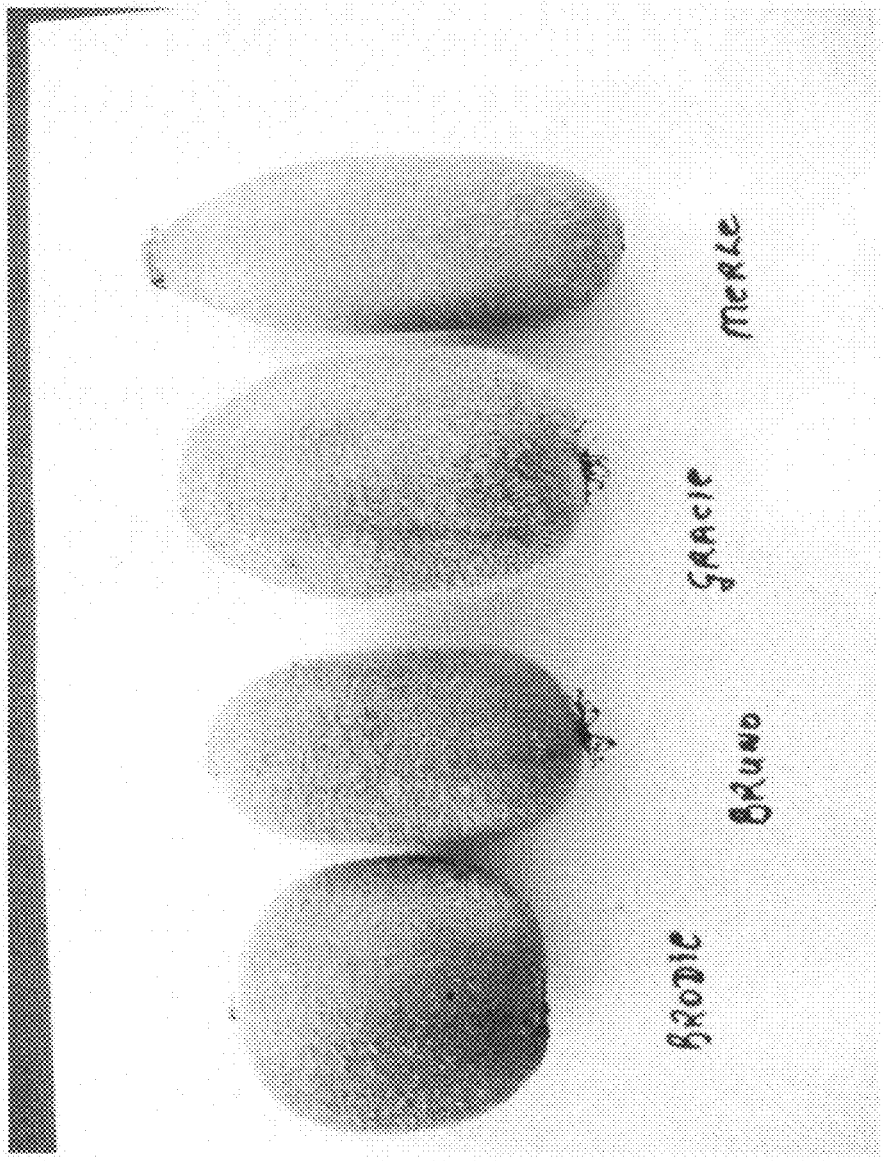

FIG. 3 contains fruits of 4 known *Actinidia* varieties, illustrating the distinct fruit shape of 'Merle'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MERLE' plants grown outdoors under commercial trial conditions in North Waikato, New Zealand. The growing temperature ranged from 10° C. to 30° C. during the day and −4° C. to 18° C. at night. Annual rainfall is approximately 125 cm per year. Measurements and numerical values represent an average of 10 typical plant types.

Botanical classification: *Actinidia deliciosa* 'MERLE'.

PROPAGATION

'MERLE' can be successfully grafted onto rootstocks of *Actnidia deliciosa.*

PLANT

*Age of the plant described.*—Approximately 5 years.
*Average height.*—180 cm.
*Average width.*—Canopy is an average of 300 cm by 400 cm to 500 cm by 500 cm. Canopy is pruned to industry standard sizing.
*Sex expression.*—Female.
*Ploidy.*—Diploid.
*Vigor.*—Moderate.
*Young shoot color.*—Near RHS Yellow-Green N144B.
*Young shoot texture.*—Smooth, non-pubescent and no visible lenticels.
*Stem diameter.*—Average 1.5 cm.
*Stem length.*—Average range 100 to 200 cm.
*Stem color.*—Near RHS Brown 200D.
*Stem texture.*—Rough.
*Trunk diameter.*—Average 5.5 cm on a 10 year old plant.
*Stem lenticels.*—Irregularly spaced and sized. Oblong in shape, color near RHS Grey-Green 191A. Length: Average range 0.25 cm to 0.5 cm. Width: Average range 0.1 cm to 0.2 cm. Density: Approximately 5 to 25 per 5 cm of stem.

FOLIAGE

Leaf:
*Average length.*—17 cm.
*Average width.*—16.5 cm.
*Shape of blade.*—Very broadly ovate.
*Apex.*—Rounded.
*Base.*—Cordate, overlapping.
*Attachment.*—Petioled.
*Margin.*—Ciliate.
*Texture of top surface.*—Slightly puckered. Non-pubescent.
*Texture of under side.*—Non-pubescent.
*Color.*—Mature foliage upper side: Near RHS Green 143A. Mature foliage under side: Near RHS Green 138B.
*Petiole.*—Length: Average length 12.5 cm. Diameter: Approximately 0.6 cm. Texture: Glabrous. Pubescence: None. Color: Upper Surface near RHS Green 143C, flushed Greyed-Red 178C. Lower surface near Greyed-Red 178D.

FLOWER

*Flowers per inflorescence.*—Normally 1, occasionally 3.
*Bud shape.*—Oblong.
*Bud color.*—Near RHS Yellow-Green 145A.
*Bud break.*—End of August.
*First flower.*—Early season, pollinizer is 'Derek'.
*Flower chill time.*—Flower chill time observed to be approximately 300 hours.
*Diameter.*—Average 6 cm.
*Depth.*—Average 3.6 cm.
*Petal quantity.*—6 to 10 per flower.
*Petals overlapping.*—Yes.

Petals:
*Length.*—Approximately 2.8 cm.
*Width.*—Approximately 2.1 cm.
*Shape.*—Spatulate.
*Aspect.*—Slightly undulating.
*Margin.*—Entire, with infrequent irregular shallow crenations.
*Texture.*—Glabrous, all surfaces.
*Base.*—Attenuate.
*Apex.*—Obtuse, retuse or sometimes with a definite notch.
*Petal color.*—Near RHS White 155A upper and lower surfaces.
*Filament color.*—Near RHS White 155A.
*Anther color.*—Near RHS Greyed-Orange 163D.
*Attitude of styles.*—Semi-erect.
*Style color.*—Near RHS White 155A.
*Style quantity.*—Average 18.
*Hair on ovary.*—Dense.
*Color of ovary.*—Near RHS White 155A.
*Number of sepals.*—6 to 10.
*Color of sepals.*—Near RHS Yellow-Green 145A upper and lower surfaces.
*Sepal width.*—Approximately 1 cm.
*Sepal length.*—Approximately 1.3 cm.
*Sepal texture.*—Smooth.
*Sepal shape.*—Deltate.
*Sepal margin.*—Entire.
*Sepal apex.*—Acute.
*Sepal base.*—Truncate.

Peduncle:
*Length.*—Average 6.6 cm.
*Diameter.*—Average 0.5 cm.
*Color.*—Near RHS Yellow-Green 145A.
*Texture.*—Smooth.

FRUIT

*Average weight.*—105 grams.
*Average length.*—10.0 cm.
*Average diameter.*—4.8 cm.
*Color outer pericarp.*—Near RHS Yellow-Green 145A.
*Color inner pericarp.*—Near RHS Yellow-Green 145B.
*Core diameter.*—Average 1.6 cm.
*Core color.*—Near RHS White 155A.
*General shape.*—Elongated obovate.
*Median cross section.*—Circular.
*Stylar end shape.*—Weakly blunt protruding.
*Shoulder shape.*—Sloped.
*Calyx ring.*—Present.
*Calyx ring expression.*—Strong.
*Skin color at harvest.*—Near RHS Yellow-Green 152C.
*Hair on fruit skin.*—Downy.
*Hair adherence to skin.*—Moderate.
*Skin adherence to flesh at maturity.*—Moderate.
*Fruit core shape.*—Transversely elliptic.
*Core-woody spike.*—Small to medium.
*Lenticels on fruit.*—Minute, moderate in quantity, colored near RHS Yellow-Green 152B.
*Locules.*—Quantity per fruit: 28. Length: Highly variable, no typical range. Width: Highly variable, no typical range. Color: Near RHS Yello-Green 145C.
*Mature seed color.*—Black.
*Dried seed.*—Brown.

Fruit stem:
*Length.*—Average range 7.8 cm to 8.3 cm.
*Diameter.*—Average 0.4 cm.
*Color.*—Near RHS Brown 200D.
*Texture.*—Smooth.
*Harvest time.*—Very early season.

OTHER CHARACTERISTICS

Storage life: Storage life is a minimum of 3 months at 2° C.
Disease/pest resistance: Neither resistance nor susceptibility to pathogens and pests common to *Actinidia deliciosa* have been observed.
Temperature tolerance: Tolerates low temperatures to approximately −5° C. without negative effects, tolerates high temperatures to approximately 35° C. without negative effects.

What is claimed is:

1. A new and distinct cultivar of *Actinidia deliciosa* plant named 'MERLE' as herein illustrated and described.

* * * * *